United States Patent
Angel et al.

(10) Patent No.: US 9,848,976 B2
(45) Date of Patent: Dec. 26, 2017

(54) ENDOPROSTHESIS, DELIVERY DEVICE AND A METHOD FOR IMPLANTING SUCH ENDOPROSTHESIS

(71) Applicant: Kardiozis, Paris (FR)

(72) Inventors: Claude Angel, Le Plessis Robinson (FR); Dominique Fabre, Le Plessis Robinson (FR)

(73) Assignee: Kardiozis, Paris (FR)

( * ) Notice: Subject to any disclaimer, the term of this patent is extended or adjusted under 35 U.S.C. 154(b) by 332 days.

(21) Appl. No.: 14/405,940

(22) PCT Filed: Jun. 5, 2013

(86) PCT No.: PCT/EP2013/061620
§ 371 (c)(1),
(2) Date: Dec. 5, 2014

(87) PCT Pub. No.: WO2013/182614
PCT Pub. Date: Dec. 12, 2013

(65) Prior Publication Data
US 2015/0148889 A1    May 28, 2015

(30) Foreign Application Priority Data
Jun. 5, 2012   (FR) ..................... 12 55207

(51) Int. Cl.
*A61F 2/06*   (2013.01)
*A61B 17/12*  (2006.01)
(Continued)

(52) U.S. Cl.
CPC .......... *A61F 2/06* (2013.01); *A61B 17/12113* (2013.01); *A61B 17/12118* (2013.01);
(Continued)

(58) Field of Classification Search
CPC ........ A61B 17/12109; A61B 17/12113; A61B 17/12118; A61B 17/12122;
(Continued)

(56) References Cited

U.S. PATENT DOCUMENTS 5,843,160 A * 12/1998 Rhodes ..................... A61F 2/07
606/194
5,935,145 A * 8/1999 Villar ............... A61B 17/12022
606/104
(Continued)

FOREIGN PATENT DOCUMENTS

DE          19531659      3/1997
EP           0647438      4/1995
(Continued)

OTHER PUBLICATIONS

Japanese Office Action issued in corresponding Japanese Patent Application No. 2015-515515 dated Dec. 20, 2016.

*Primary Examiner* — Dianne Dornbusch
(74) *Attorney, Agent, or Firm* — Davis & Bujold PLLC; Michael J. Bujold

(57) ABSTRACT

The invention relates to an endoprosthesis (1), in particular a vascular or cardiac endoprosthesis (1), having a body (2) and also one or more thrombogenic elements (3) that are fixed to the endoprosthesis (1) and that are able to extend a distance away from the body outside the latter. The endoprosthesis comprises means (33) for selectively retaining the thrombogenic elements near the body (2). The release of the one or more thrombogenic elements, after the endoprosthesis has been fitted in place by a conventional method via a sheath, promotes thrombosis.

34 Claims, 10 Drawing Sheets

(51) Int. Cl.
*A61F 2/07* (2013.01)
*A61F 2/24* (2006.01)
*A61F 2/966* (2013.01)
*A61F 2/82* (2013.01)
*A61F 2/848* (2013.01)

(52) U.S. Cl.
CPC .......... *A61B 17/12122* (2013.01); *A61F 2/07* (2013.01); *A61F 2/2418* (2013.01); *A61B 17/1215* (2013.01); *A61F 2/966* (2013.01); *A61F 2002/065* (2013.01); *A61F 2002/067* (2013.01); *A61F 2002/077* (2013.01); *A61F 2002/825* (2013.01); *A61F 2002/8483* (2013.01); *A61F 2210/0004* (2013.01); *A61F 2220/0008* (2013.01); *A61F 2220/0016* (2013.01); *A61F 2230/005* (2013.01); *A61F 2230/0054* (2013.01); *A61F 2230/0065* (2013.01); *A61F 2250/006* (2013.01); *A61F 2250/0059* (2013.01); *A61F 2250/0067* (2013.01); *A61F 2250/0069* (2013.01); *A61F 2250/0071* (2013.01)

(58) Field of Classification Search
CPC .......... A61B 17/1215; A61F 2/04; A61F 2/06; A61F 2/07; A61F 2002/065; A61F 2002/072; A61F 2002/075; A61F 2002/077
See application file for complete search history.

(56) References Cited

U.S. PATENT DOCUMENTS

| | | | | |
|---|---|---|---|---|
| 6,730,119 | B1* | 5/2004 | Smalling | A61F 2/07 606/194 |
| 2002/0169473 | A1* | 11/2002 | Sepetka | A61B 17/12022 606/200 |
| 2003/0004568 | A1* | 1/2003 | Ken | A61B 17/12022 623/1.46 |
| 2003/0040771 | A1* | 2/2003 | Hyodoh | A61F 2/90 606/200 |
| 2004/0098023 | A1* | 5/2004 | Lee | A61B 17/12022 606/200 |
| 2007/0207179 | A1* | 9/2007 | Andersen | A61B 17/12022 424/423 |
| 2008/0027531 | A1* | 1/2008 | Reneker | A61B 17/12022 623/1.15 |
| 2008/0275536 | A1 | 11/2008 | Zarins | |
| 2011/0022153 | A1 | 1/2011 | Schreck et al. | |

FOREIGN PATENT DOCUMENTS

| | | |
|---|---|---|
| JP | 2000279533 A | 10/2000 |
| WO | 00/18325 | 4/2000 |
| WO | 01/66167 | 9/2001 |
| WO | 2006/111801 | 10/2006 |
| WO | 2009/149294 | 12/2009 |

* cited by examiner

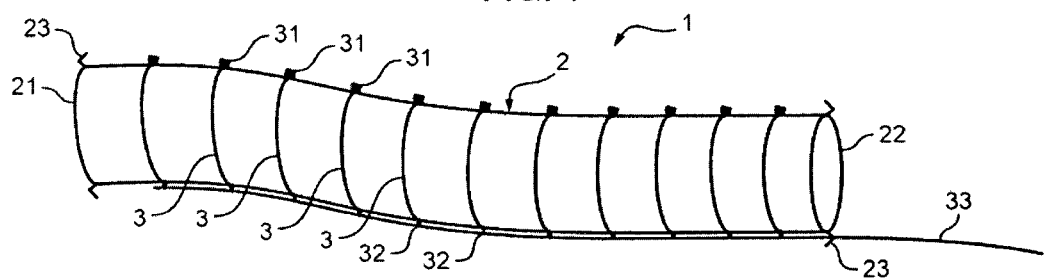
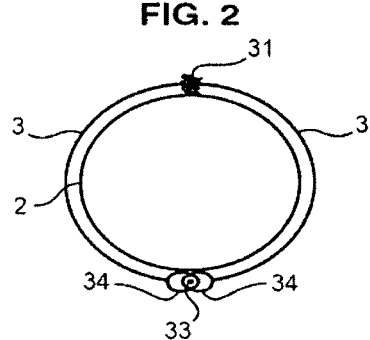
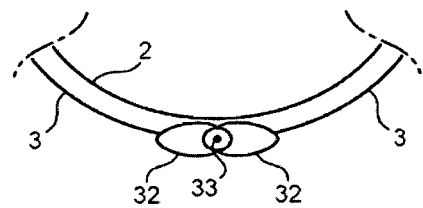
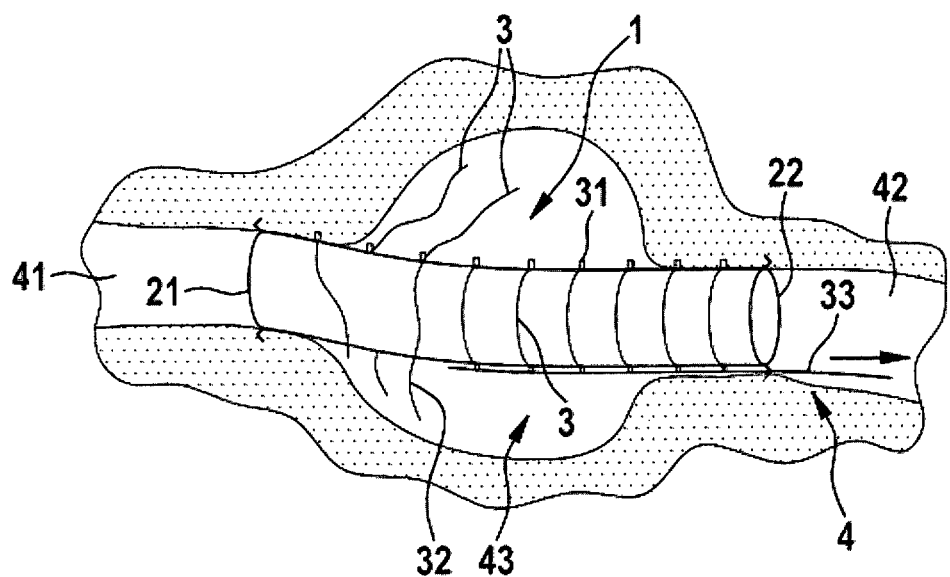

ENDOPROSTHESIS, DELIVERY DEVICE AND A METHOD FOR IMPLANTING SUCH ENDOPROSTHESIS

TECHNICAL FIELD

The present invention relates to the field of endoprostheses such as stents, and more particularly to endoprostheses combined with thrombogenic elements.

BACKGROUND ART

Endoprostheses composed of a sheath armed with one or more elements of the stent type are commonly used for the treatment of arterial aneurysms, in order to re-establish the geometry of the artery.

In a well-known procedure, an endoprosthesis is positioned in such a way that it isolates the aneurysm from the blood flow in order to prevent growth of the aneurysm.

However, in a considerable number of cases, it has been observed that the aneurysm continues to grow on account of its being irrigated by blood vessels other than the artery concerned. The risk of rupture therefore remains.

In an attempt to address this problem, solutions have already been proposed that involve introducing thrombogenic materials into the aneurysm after the endoprosthesis has been fitted in place, or even at the same time as the endoprosthesis is being fitted in place, in order to promote thrombosis of the aneurysm and thereby avoid any risk of rupture.

However, the introduction of these thrombogenic materials is an awkward procedure and greatly complicates the interventions, especially as it is necessary to ensure that these thrombogenic materials do not obstruct the fitting of the endoprosthesis and that they remain exclusively outside the endoprosthesis and do not risk penetrating the inner conduit of the latter.

DISCLOSURE OF THE INVENTION

The object of the present invention is therefore to overcome the advantages of the prior art and in particular to provide an endoprosthesis, a delivery device and a delivery method which allow to avoid a continued grow of aneurysms and which allow in particular to use thrombogenic materials easily and without risks to the patient.

The invention thus relates to an endoprosthesis, in particular a vascular or cardiac endoprosthesis, having at least one body and also one or more thrombogenic elements that are fixed to the endoprosthesis and that are able to extend a distance away from the body outside the latter. The endoprosthesis may be formed integrally as one body part or preferably may be formed of more than one body part which are attachable to each other. According to a first aspect of the invention, at least one area of the outer surface of the at least one body part of the endoprosthesis, preferably the whole outer surface of the at least one body part of the endoprosthesis is provided with thrombogenic elements which are substantially uniformly distributed over the at least one area of the outer surface, preferably over the whole outer surface. In context with the present application, a substantially uniform distribution over the surface is understood to refer to a coverage of at least 50% of the surface by thrombogenic elements. By providing thrombogenic elements substantially uniformly over the surface of the body it can be made sure that thrombogenic elements will be arranged in the area where the aneurysms is located. Since the thrombogenic elements are directly provided on the body of the endoprosthesis, there is no risk of migration of the elements into the blood flow.

In some embodiments the thrombogenic elements might only be arranged in an area of the outer surface. E.g. in cardiac stents, the thrombogenic elements are only arranged on the outer surface of an upstream area of the endoprosthesis. In an aortic valve, the thrombogenic elements are therefore only arranged on the ventricle side of the stent. The thrombosis effect of the thrombogenic elements will permit a reduction of paravalvular leakage. As the aortic side is free of thrombogenic elements, there is no increased risk of a thrombus migration with the blood stream. In a mitral valve, the thrombogenic elements would therefore be arranged on the atrium area and not in the ventricle area of the outer surface.

A further aspect refers to an endoprosthesis, in particular a vascular or cardiac endoprosthesis, having a body and also one or more thrombogenic elements that are fixed to the endoprosthesis so that the elements are able to extend a distance away from the body outside the latter.

According to this aspect of the invention the emdoprosthesis comprises means for selectively retaining the thrombogenic elements near the body.

Preferably the thrombogenic elements are formed by fibres. Fibres are highly thrombogenic. They automatically expand in the presence of blood. The flexibility of fibres also allows an arrangement in any desired manner, e.g. in certain directions along the endoprosthesis.

The thrombogenic elements may be elongate and can be each connected to the body by an anchoring point. They are able to deploy from this anchoring point. By attachment of each thrombogenic element at an anchoring point, the position of the thrombogenic elements can be easily and independently chosen. Furthermore, a complete separation of the thrombogenic elements from the body is avoided.

According to another aspect of the invention there is provided an endoprosthesis having thrombogenic elements. Thrombogenic elements are arranged at least partially on the outer surface of the prosthesis. The endoprosthesis is further provided with at least one selectively deactivatable retaining element. The retaining element is used for retaining the thrombogenic elements near the surface of the body part. Retaining the elements near the surface of the body part is understood as keeping the elements closer to the surface when the retaining means are not yet deactivated and allowing the thrombogenic elements to move away from the surface at a further distance upon deactivation. With such selectively deactivatable retaining elements obstructions during the fitting of the endoprosthesis may be avoided.

If the thrombogenic elements are connected to the body by an anchoring point, the thrombogenic elements can easily deploy radially or axially away from said anchoring point.

The thrombogenic elements can be formed as loops at least locally. In this case, the retaining elements may comprise at least one alonged retaining element which passes through these loops and which is able to be removed from the loops. By removing the alonged retaining element e.g. by pulling in one direction, the thrombogenic elements can be released and deployed. Preferably, these loops are situated in the area of the free ends of the thrombogenic elements. This makes manufacturing particularly easy.

It is also possible to form loops along substantially the entire length of the thrombogenic elements by using filament like thrombogenic elements fixed at both of their free ends. A loop is automatically formed substantially along the entire length of such filament. In this case, an alonged retaining element preferably passes through a zone where at least two loops of two separate thrombogenic elements cover each other, i.e. partly overlap. The retaining elements may have preferably a length chosen such that it is possible to pull the retaining element through a sheath of a delivery device which is used for insertion of the endoprosthesis, e.g. which can be pulled through a catheter.

If one retaining means retains at least two, preferably all, thrombogenic elements in position, more than one and preferably all thrombogenic elements can be deployed by actuation of one retaining means.

Preferably, the retaining means can be deactivated by being torn towards a proximal end of a delivery system. The proximal end of the delivery system is the end which is directed towards the operator.

According to an alternative embodiment, the selectively deactivatable retaining means is formed of a resorbable material. Upon contact with body fluids after deployment, the retaining means are gradually resorbed and thereby deactivated. Once the retaining means are resorbed, the thrombogenic elements are released. Consequently, in context with the present application, selective activation or deactivation not only refers to elements which require actuation by the operator but also include elements which automatically are deactivated under certain conditions, e.g. upon contact with certain materials or upon change of temperature.

According to still an alternative embodiment, the selectively deactivatable elements may comprise a tearable envelope. The elements may be deactivated through tearing this envelope or by pulling it away, e.g. in an axial direction, preferably proximally but also distally.

It is possible to provide the thrombogenic elements with at least one medical substance and to design the elements such as to deliver the substance once the endoprosthesis has been implanted.

The body of the endoprosthesis may be formed tubularly and the thrombogenic elements may extend circumferentially around the body. It is, alternatively, also possible to use thrombogenic elements which extend axially along the body. Also, combinations of these embodiments are possible, i.e. the thrombogenic elements may be arranged helically or some of the elements may be arranged axially and others circumferentially.

According to a preferred embodiment of the invention, the outer surface of the at least one body may have at least one edge area which is free from thrombogenic elements. If edge areas are not provided with thrombogenic elements, the attachment of other structural elements on the edge area may be facilitated. Furthermore, extension of the thrombogenic elements over the edge area may be prevented.

The areas without thrombogenic elements at the distal ends further avoid distal thrombosis.

It is advantageous to attach the thrombogenic elements on the surface at a place and to choose the size of the thrombogenic elements such that they do not extend over an axial edge of the body part. Extension of the thrombogenic elements into the blood flow once the endoprosthesis is implanted thereby may be prevented.

It is possible to design the endoprosthesis as a bifurcated endoprosthesis which comprises two body parts. In particular, such bifurcated prosthesis comprise a main part and a leg which is attached or attachable to the main part. It is, also possible to design the endoprosthesis as a trifurcated endoprosthesis which comprises three parts such as a main part and two legs attached or attachable to the main part. Such bifurcated or trifurcated endoprostheses are known to the skilled person. For attachment of the legs to the main part, the main part and the legs may be provided with an attachment portion(s). This attachment portion preferably may be truncated. Preferably, the attachment portion of the leg and/or the main body has an edge area which is free from thrombogenic elements. Also, the complete attachment portion preferably may be free from thrombogenic elements.

When attached to each other, one inner attachment portion is radially covered on its outer surface by the other attachment portion. In particular the inner attachment portion is free from thrombogenic elements. The absence of thrombogenic elements in such areas facilitates attachment of the legs on the main part. Since the attachment portion on the main body will be covered by the legs (or vice versa the secondary portion will be covered by the legs), thrombogenic elements arranged in such area would not have an effect anyhow.

According to a further preferred embodiment, thrombogenic elements may be provided on the main part and the legs preferably may be free from thrombogenic elements.

While a preferred indication of the endoprosthesis as disclosed above is the treatment of aneurysms, the skilled person will appreciate that the use of such prosthesis as stent valves may also be advantageous. In particular, the endoprosthesis may be able to be placed in the area of a pre-existing cardiac valve and may allow to restore the valve function. The thromboses caused by the thrombogenic elements may permit a reduction in para valvular leaks.

According to still another aspect of the invention there is provided a delivery device which comprises an endoprosthesis as disclosed above. The delivery device has preferably at least one sheath configured to keep the endoprosthesis compressed during delivery. The endoprosthesis is arranged such as to be released through a relative movement between the sheath or the sheaths and the endoprosthesis.

In a preferred embodiment, the device may further be provided with an activation mechanism for deactivating a retaining element retaining the thrombogenic elements near the endoprosthesis. It is, however, also possible to use retaining elements which are automatically deactivated upon implantation.

Still another aspect of the invention refers to a method for implanting an endoprosthesis as described above. The endoprosthesis is particularly implanted in a vascular site having aneurysms or near a native cardiac valve. In a first step, the endoprosthesis is positioned at the site in such a way as to isolate aneurysms from the blood flow or at the site neighbouring the native valve.

In a next step, the thrombogenic elements of the endoprosthesis are released in such a way that they extend a distance away from the endoprosthesis into the aneurysms or towards the wall neighbouring a native valve.

The thrombogenic elements may be formed as filaments attached to the surface of the body, e.g. filaments made of natural materials such as cotton, silk or synthetic materials such as Dacron, polyesters or polyamides. Typically individual filaments may be used. It is also possible to use bamboos of a plurality of filaments, e.g. 5:100 filaments.

BRIEF DESCRIPTION OF THE FIGURES

Other features, aims and advantages of the invention will become clear from the following description which is purely illustrative and non-limiting and which is to be read with reference to the attached drawings, in which:

FIG. 1 is a side view of a first embodiment of a vascular endoprosthesis according to the invention, FIG. 2 is a sectional view, in a transverse plane, of the endoprosthesis from FIG. 1;

FIG. 3 illustrates a detail from FIG. 2 in an enlarged view;

FIG. 4 illustrates the placement of such an endoprosthesis;

In all of the figures, similar elements are designated by common reference numbers.

DETAILED DESCRIPTION

Figure 5:
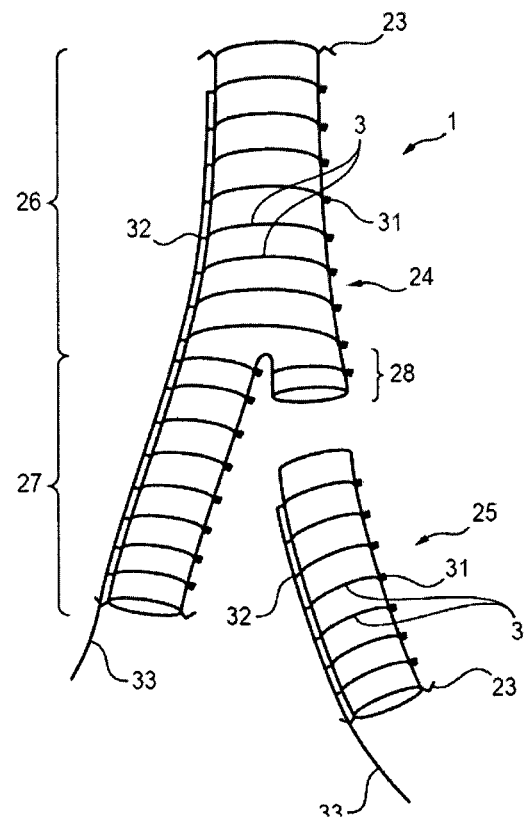
FIG. 5 illustrates another example of an endoprosthesis according to the invention.

FIG. 1 shows an example of an endovascular prosthesis 1 which is of the type composed, for example, of a stent in one or more parts sutured to a tubular sheath typically made of polyester, and which is typically used for the treatment of an aneurysm in a blood vessel or an artery. It could also be a prosthesis of the cardiac valve type for example, and more generally any endoprosthesis in which it is desirable to obtain a thrombosis effect outside the endoprosthesis after it has been fitted in place.

FIG. 2 shows a sectional view of the vascular endoprosthesis 1.

The endoprosthesis 1 as shown is composed of a tubular body 2 that extends between a proximal end 21 and a distal end 22 and that is formed by the combination of the stent and its sheath.

The ends 21 and 22 of the endoprosthesis 1 are typically provided with anchoring means 23 such as anchoring hooks or barbs that are formed on the stent part and that are designed to hook themselves in tissues of the walls of the blood vessel in question, thereby ensuring that the endoprosthesis 1 is maintained in position in this vessel.

The endoprosthesis 1 is provided with thrombogenic elements 3, here filaments, which are fixed to the outside thereof and extend near the outer surface of the tubular body 2.

In the embodiment shown, the thrombogenic filaments 3 are arranged so as to form rings around the body 2 of the endoprosthesis 1 and are typically distributed uniformly along the length thereof. The filaments 3 can be arranged so as to surround the body 2 one or more times.

The thrombogenic filaments 3 are each connected to the body 2 of the endoprosthesis by an anchoring point 31 (preferably on the stent part) of the body, the filament between this anchoring point 31 and its free end 32 being able to deploy a distance away from the body 2 of the endoprosthesis 1 starting from this anchoring point 31. Alternatively, one and the same filament can be anchored in an intermediate region of its length, the filament then forming two strands that are able to deploy between the common anchoring point 31 and their respective free ends.

Advantageously, the thrombogenic filaments 3 are maintained in contact with the body 2 by temporary retaining means 33.

These temporary retaining means 33 are designed to selectively release said thrombogenic filaments 3 in such a way that the latter deploy around the body 2 of the endoprosthesis 1, while at the same time ensuring that they are maintained against the body 2 of the endoprosthesis 1 prior to, and in particular during, the placement of the endoprosthesis.

In the embodiment shown, the temporary retaining means comprise a cord 33 in engagement with the free ends 32 of the thrombogenic filaments 3, these free ends 32 in this case having, for example, loops or eyelets 34 through which the cord 33 is passed.

It will be understood that by pulling the cord 33 in the longitudinal direction of the endoprosthesis 1, so that it detaches from the loops 34, thrombogenic filaments 3 then become free to deploy a distance away from the body 2 of the endoprosthesis 1, while at the same time remaining connected to the latter via their respective anchoring point 31.

FIG. 3 shows a detailed view of the free ends 32 of the thrombogenic filaments 3 comprising loops 34 through which a cord 33 passes. The loops can be made from the filament itself, with a knot or a weld point, or can be formed by an attached element such as a small ring.

FIG. 4 illustrates such an endoprosthesis 1 in place in a vessel such as an artery.

In this figure, the vessel 4, for example an artery, is shown with an aneurysm 43 located between a proximal portion 41 and a distal portion 42 of the vessel.

The endoprosthesis 1 is positioned in the vessel 4 in such a way as to isolate the aneurysm 43 from the blood flow, that is to say to connect the proximal portion 41 directly to the distal portion 42.

The proximal end 21 and the distal end 22 of the endoprosthesis 1 are connected respectively to the proximal portion 41 and to the distal portion 42 of the vessel 4 via their anchoring arrangements 23.

The blood in the vessel 4 thus flows through the endoprosthesis 1 without passing through the aneurysm 43.

The implantation of the endoprosthesis 1 in the vessel 4 can be performed using any suitable technique. A person skilled in the art is aware in particular of the implantation techniques performed with the aid of an insertion sheath or by means of a balloon, which are commonly used techniques.

Figure 7:
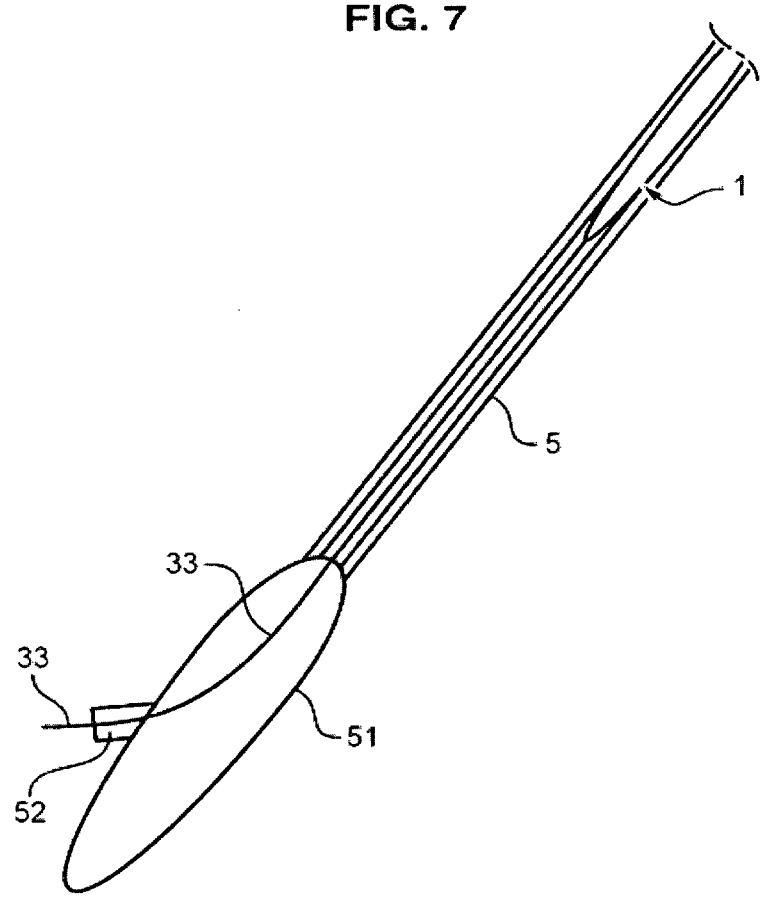
FIG. 7 is a diagrammatic and perspective view illustrating the endoprosthesis from FIGS. 1 to 4 in an insertion sheath.
Figure 9:
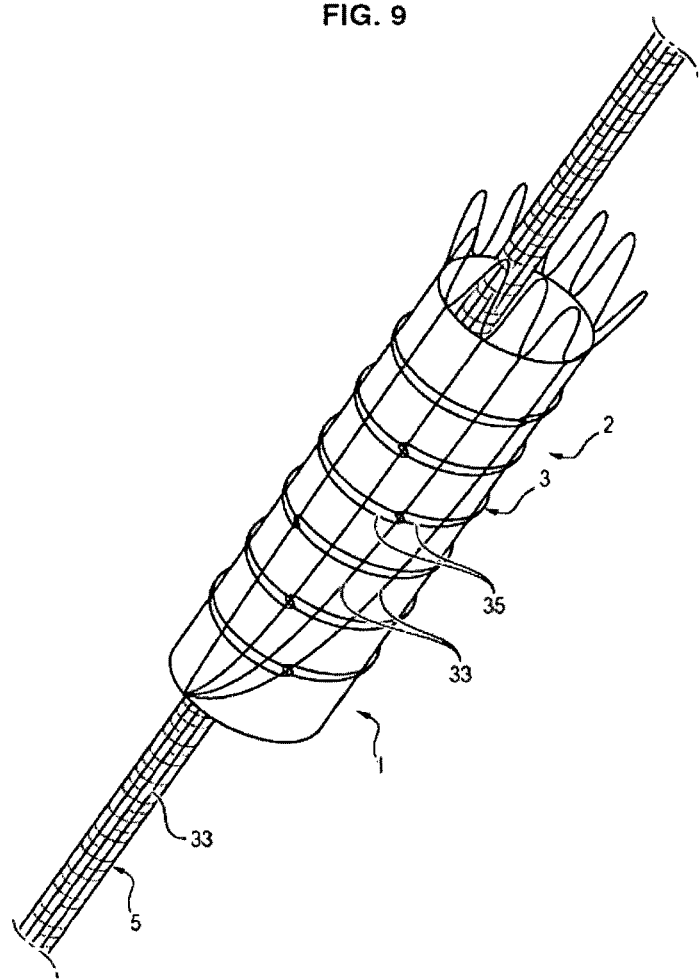
FIGS. 9 to 12 illustrate an endoprosthesis according to a variant of the invention.
Figure 10:
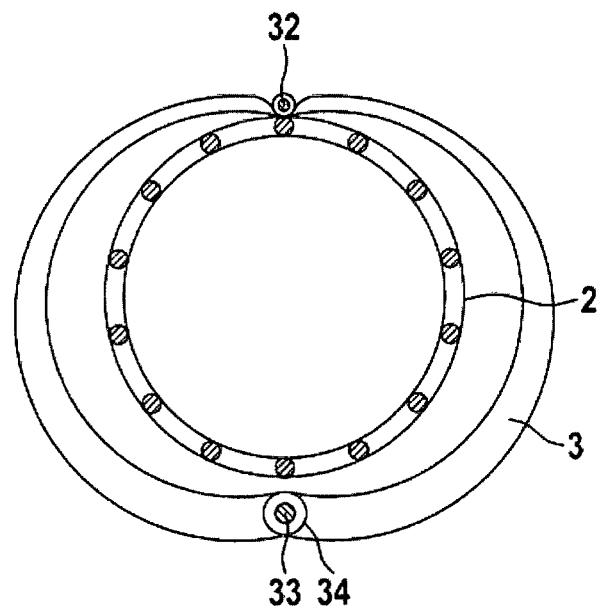
Figure 11:
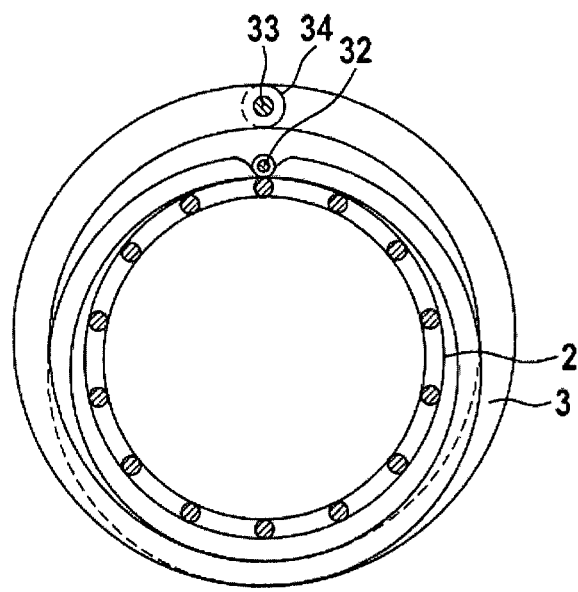

With reference now to FIG. 7, in the case where the endoprosthesis is introduced with the aid of an insertion sheath 5 which keeps the endoprosthesis 1 compressed during the phase of insertion, the cord 33 extends along the sheath 5 as far as a handle 51 and through a passage 52 from which the cord emerges to the outside.

Figure 8:
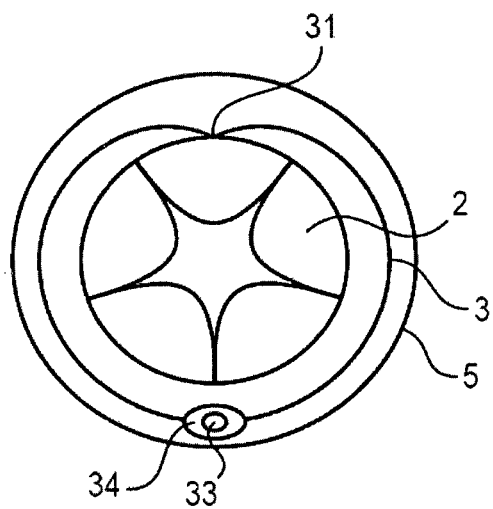
FIG. 8 shows a transverse section of the endoprosthesis from FIGS. 1 to 4 in an insertion sheath.

FIG. 8 illustrates the endoprosthesis 1 provided with filaments 3 and composed inside the sheath 5, in which the cord 33 also extends.

Once the endoprosthesis 1 has been positioned in the vessel 4, the practitioner applies traction to the cord 33 protruding from the opening 52, in such a way that loops 32 detach from the thrombogenic filaments 3, thereby releasing the latter, and these can then deploy a distance away from the endoprosthesis 1, especially within the volume of the aneurysm 43.

This deployment of the thrombogenic filaments 3 in the aneurysm 43 will bring about thrombosis within the volume of the aneurysm 43 and thereby prevent continued development of the latter.

The endoprosthesis 1 as shown thus permits simple deployment of thrombogenic elements in the aneurysm after the endoprosthesis has been positioned in the vessel, and it does this without the filaments interfering with this positioning by means of the sheath 5 or without the filaments penetrating into the inner conduit of the endoprosthesis 1.

FIG. 5 shows another embodiment of an endoprosthesis 1 according to the invention.

In this embodiment, the endoprosthesis is a bifurcated endoprosthesis with a body 2 composed of two parts, namely a main part and an attached leg, in a manner known per se.

The main part 24 has several portions of defined dimensions, namely a common tubular portion 26 which then divides into two secondary tubular portions 27 and 28 of smaller dimensions, one of these secondary portions 28 being truncated and designed to join to the attached leg 25 in order to form the bifurcated structure of the endoprosthesis.

As in the embodiment shown in the preceding figures, the body 2 of the endoprosthesis 1 is provided with thrombogenic filaments 3 arranged in rings around the different portions of the main part 24 and of the attached part 25. These thrombogenic filaments 3 are connected to the body 2 at respective anchoring points 31 and thus form strands which have a free end 32 and which are able to deploy a distance away from the body 2 of the endoprosthesis 1, starting from their respective anchoring point 31. The free ends 32 in the shape of a loop or eyelet are maintained in position by temporary retaining means 33, for example in this case once again by a cord 33 that can be pulled in order to release the free ends 32 of the filaments 3, as has been described above.

It will be noted that, in view of the particular structure of the endoprosthesis 1 which here comprises a body 2 in two parts, several temporary retaining arrangements 33 are necessary, in this case one retaining arrangement 33 for the main part 24 and one retaining arrangement 33 for the attached part 25.

Alternatively and depending on the area where the aneurysms are located, it is also possible to provide the thrombogenic filaments only on the main part 24 or only on the leg 25. Furthermore, it is possible to provide an area on the secondary tubular portion 28 without any thrombogenic elements or to provide an end area of the leg 25 without any thrombogenic elements. Such areas free from thrombogenic elements allow a better attachment of the leg 25 to the main part 24 without the risk of thrombogenic elements entering in the interior of the endoprosthesis.

The implantation of the endoprosthesis 1 from FIG. 5 is performed in the conventional way, while the thrombogenic filaments are retained against the respective bodies of the parts 24 and 25. The parts 24 and 25 are fitted in place one after the other and then joined.

Once they have been thus joined in order to form the bifurcated structure of the endoprosthesis, the practitioner pulls on the temporary retaining means 33 in order to allow the thrombogenic filaments 3 to deploy a distance away from the endoprosthesis.

It will be clearly appreciated here that an additional advantage of the selective and controlled deployment of the thrombogenic filaments, which are only deployed once the body 2 of the endoprosthesis is positioned and assembled, is that it is possible to avoid the thrombogenic filaments 3 of one part of the endoprosthesis penetrating into the inner conduit of the other part when they are being joined.

Figure 6:
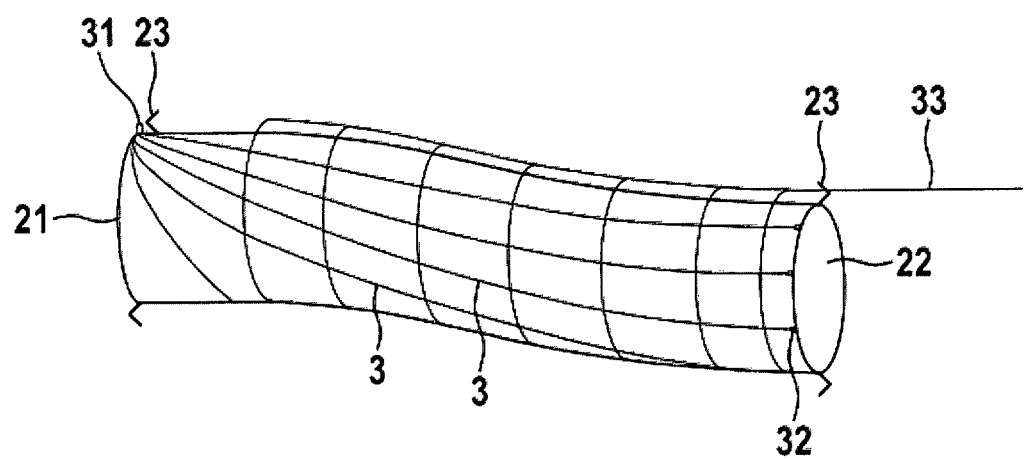
FIG. 6 shows yet another example of an endoprosthesis according to the invention.

FIG. 6 shows another example of the arrangement of the thrombogenic filaments 3 on the outer surface of an endoprosthesis 1.

In this embodiment, the thrombogenic filaments 3 are fixed to the body 2 of the endoprosthesis 1 by a common anchoring point 31 arranged at one of the ends, in this case the proximal end 21, and extend as far as the other end, in this case the distal end 22, in such a way that they are distributed about the whole periphery of the endoprosthesis 1.

Here, the temporary retaining means are also composed of a cord 33 which forms a plurality of rings distributed along the body 2 of the endoprosthesis 1, in such a way as to keep the thrombogenic filaments against the body 2 of the endoprosthesis 1 for as long as these retaining means 33 are present.

When the filaments 3 are to be deployed, the retaining means 33 are withdrawn, typically by pulling the cord 33 which will thus come loose from the body 2, for example ring by ring, thus progressively releasing the thrombogenic filaments 3 such that the latter deploy a distance away from the endoprosthesis 1.

It will be appreciated that many variants are possible as regards the configuration of the thrombogenic filaments 3 on the body 2 of the endoprosthesis and as regards the retaining arrangements.

With reference to the embodiment shown in FIG. 6, it is thus possible to arrange several groups of thrombogenic filaments 3 on the endoprosthesis 1, for example two groups similar to the one illustrated in FIG. 6, each starting from one end of the endoprosthesis 1 and each having a common anchoring point 31.

It is also possible, for example, to combine the embodiments shown in FIGS. 1 and 5, in which case the thrombogenic filaments 3 arranged in rings, as shown in FIG. 1, are able to maintain the thrombogenic filaments arranged longitudinally, as shown in FIG. 6.

With reference now to FIGS. 9 to 12, an alternative embodiment has been shown in which each thrombogenic filament is formed by a loop closed on itself. This can be achieved, for example, by fastening each free end of an individual filament at a common anchoring point, or at two anchoring points near each other. In this case, the temporary retention is provided by a cord passing through the loop formed by the assembly of the filament 3 near the site where the filament changes direction to return to the anchoring region. As is illustrated, the preferred configuration here is one in which two filaments in a loop shape extend through approximately 180° about the body 2 on each side thereof, the retention cord 33 passing through the loops formed by the two filaments in an end region where these loops straddle each other.

Figure 12:
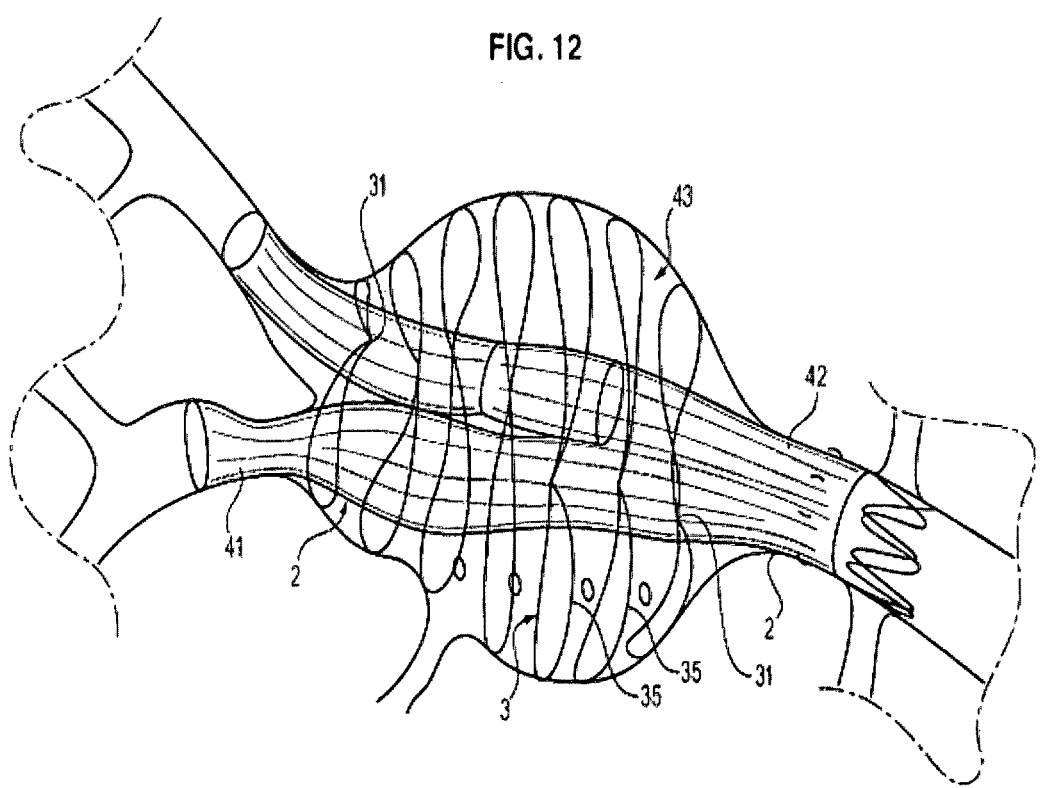

FIG. 12 illustrates the endoprosthesis in place, after deployment of the loop-shaped filaments in the aneurysm 43.

Figure 13:
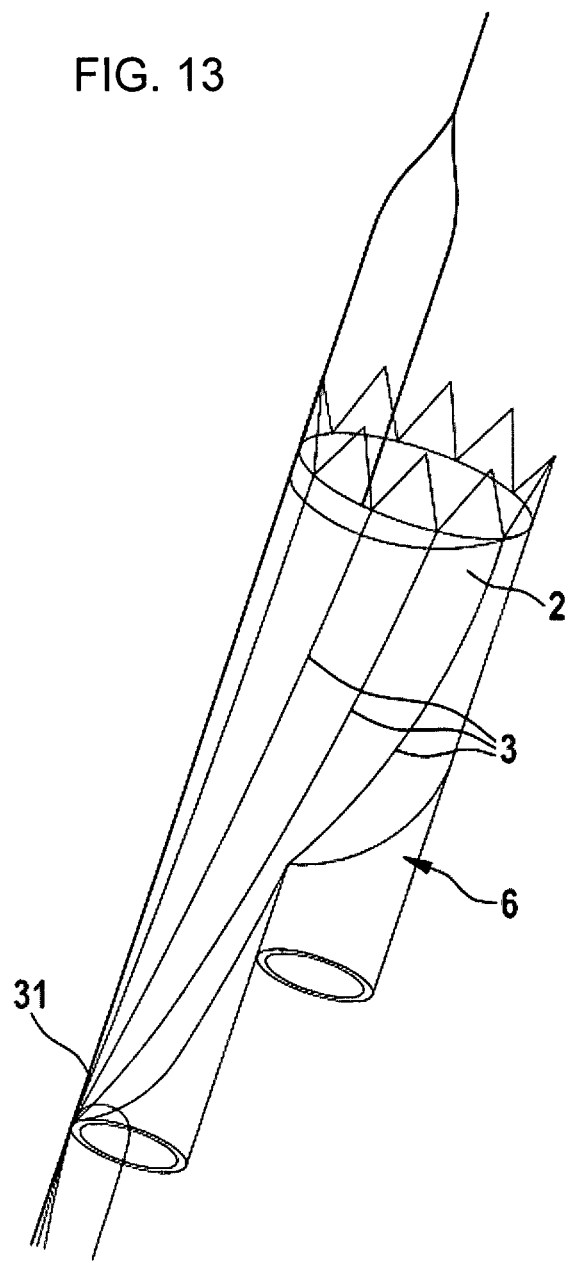
FIG. 13 is a diagrammatic and perspective view of an endoprosthesis according to another embodiment of the invention.

FIG. 13, finally, shows a diagrammatic view of another embodiment in which thrombogenic filaments 3 extend in the general longitudinal direction of a main part of a bifurcated vascular endoprosthesis, starting from two anchoring points situated at a proximal end of said main part and in the area of the bifurcation to the attached leg.

In this embodiment, the means for retaining the filaments comprise an envelope 6 that entirely surrounds the endoprosthesis and the filaments and that can be torn and removed in situ after the endoprosthesis has been fitted in place.

Figure 14:
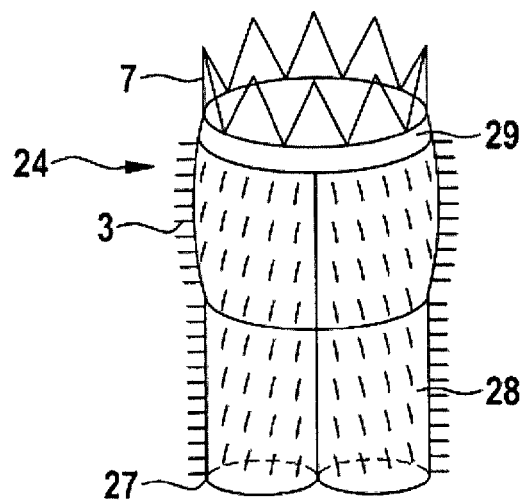
FIG. 14 is a schematic side view of another preferred embodiment of a vascular prosthesis according to the invention and FIG. 15 is a side view of a leg attachable to a main body of a bifurcated or trifurcated endoprosthesis.

FIG. 14 schematically shows a main body 24 of a trifurcated endoprosthesis 1. The main body 24 comprises a common tubular section 26 and two equally long secondary tubular portions 27, 28. The tubular portions 27, 28 form an overlap zone for receiving a respective leg 25 (see also FIG. 15) of the trifurcated prosthesis. The main part 24 is typically made relatively short with a common tubular section 26 of typically 4 cm in axial direction and with a length of the secondary tubular portions 27, 28 of about 3 cm.

The axially upper, i.e. proximal edge of the common tubular section 26 has an area 29 which is not provided with thrombogenic elements. A suprarenal stent 7 is arranged at the proximal edge of the common tubular section. Since no thrombogenic elements are arranged in the area 29, extension of the thrombogenic elements into the interior of the endoprosthesis is prevented even after release of the thrombogenic elements. For this purpose, the length of the thrombogenic elements is chosen depending from the position where there are arranged and depending on the axial length of the area 29. Typically, the length of the thrombogenic elements should be chosen shorter than the axial distance between the anchoring point of the respective element and the proximal edge of the common tubular section. Typically, the fibres can have a length of several mm up to 5 cm and the distance between the fibres is about 3 mm. The thrombogenic elements are very short i.e. several millimeters near the distal and proximal end of the prosthesis and the longest i.e. about 5 cm at about the centre of the prosthesis. A possible distribution of the length of the thrombogenic elements is shown and detailed in FIG. 19.

The common tubular section 26 and the secondary tubular portions 27, 28 are substantially uniformly provided with thrombogenic elements in the form of fibres.

Figure 15:
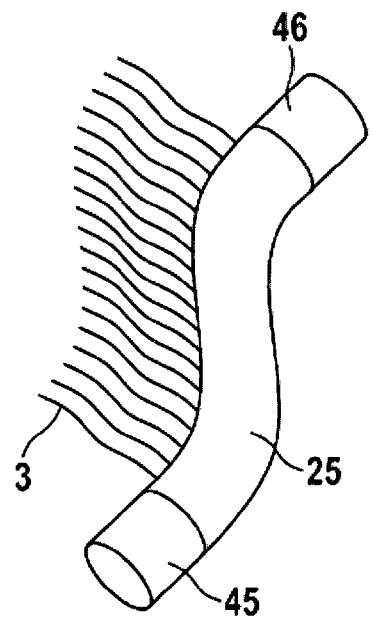

FIG. 15 schematically shows a leg 25 which can be attached to one of the secondary tubular portions 27, 28 shown in FIG. 14. The leg 25 is provided with thrombogenic elements in the form of fibres along its length. The distal end 45 and the proximal end 46 of the leg 25 are again provided with an area without thrombogenic elements. The area at the proximal end 46 has a length corresponding substantially to the length of the secondary portion of the main part 24 to which the leg 25 should be attached. If e.g. a main part 24 as shown in FIG. 14 with a secondary tubular portion 27, 28 having an axial length of 3 cm is chosen, the length of the overlap in the area close to the end 46 is also 3 cm. The distal end 45 of the leg 25 is also provided with an area without thrombogenic elements. The area without thrombogenic elements neighbouring the proximal end 46 is advantageous in context with the attachment of the leg 25 to the main part 24. In particular, such an area may exclude that thrombogenic elements extent into the interior of the assembled endoprosthesis. The legs typically have a length of about 12 mm.

Alternatively, if the leg is attached over the secondary portion, the proximal end area of the leg 25 may be provided with thrombogenic elements whereas the distal end of the secondary portion is free from such elements. The area without thrombogenic elements at the distal end 45 prevents extension of thrombogenic elements over the axial end of the endoprosthesis and thus prevents extension of thrombogenic elements into the blood flow.

In a further alternative embodiment, instead of retaining means 33 in the form of a wire extending out of a delivery device, the retaining means may be simply formed of a resorbable material. A cord attaching the thrombogenic elements similar as shown in FIGS. 2/3 may be made of a resorbable material. Once the endoprosthesis is implanted, the resorbable retaining means are resorbed after a certain period of time and the thrombogenic elements are released. The time might be rather short, i.e a range of a few minutes or hours or it might take some time to resorb the material i.e. a couple of month or any time in between. A separate actuation by the operator is therefore not necessary.

The thrombogenic elements typically are formed as filaments having a length of several mm up to 5 cm and made of natural fibres such as cotton or of silk.

The endoprosthesis, e.g. the main body 24 further may be provided with radio opaque markers, e.g. along the circumference of the distal end or the proximal end.

The suprarenal stent 7 may be provided with hooks for better fixing of the endoprosthesis at the implantation site. The main body per se may be provided without any hooks. The axial length of the suprarenal stent is chosen to be relatively short e.g. typically about 2.3 cm. The endoprosthesis is formed in a manner known to the skilled person, i.e. typically with a support structure made of a nitinol stent having a plurality of circumferentially running zick-zack shaped members which are sutured on a tubular sleeve made of a polymeric material.

Figure 16:
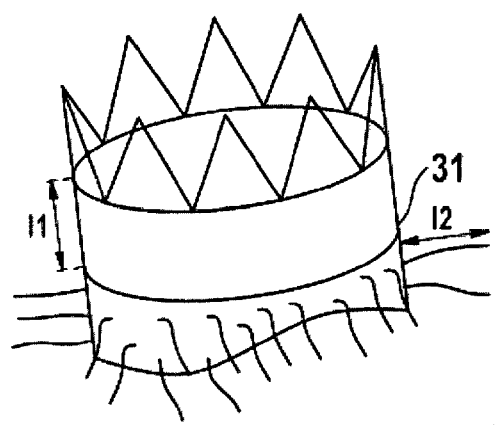
FIG. 16 is an enlarged view of the proximal end of the embodiment shown in FIG. 14.

FIG. 16 schematically shows an enlarged view of the proximal end of the main part 24 as shown in FIG. 14. The main part 24 has the area 29 without thrombogenic elements having a length 11 of typically about 1.4 cm. Thrombogenic elements in the form of filaments 3 are attached at an anchoring point 31 with one end and have another free end. The length 12 between the anchoring point 31 and the free end is shorter than the length 11.

Of course, the present invention is not limited in any way to the embodiments that are described and illustrated, and instead numerous variants are possible.

As regards the materials, the endoprosthesis can be made with the usual materials for its sheath and the one or more stents composing it, while the thrombogenic filaments are made, for example, of natural fibres such as cotton or silk or of polyester or another biocompatible polymer.

The one or more cords 33 can be made of polymer with a suitable cross section and tensile strength if they are intended for manual actuation. In this case it is not essential for them to be biocompatible since they do not remain at the implantation site. In the embodiment in FIG. 13, the envelope 6 can also be made of polymer, for example a low-density polymer in order to be able to break open.

Moreover, the thrombogenic elements in the form of filaments can be replaced by any other generally elongate elements that are able to extend away from the body 2 of the endoprosthesis, for example tapes, tubes, etc.

Finally, it will be noted that the thrombogenic elements can be treated in such a way as to deliver a drug on site.

As was mentioned at the start of the description, the invention can also be applied in particular to a cardiac endoprosthesis comprising a stent and valvules, which is delivered to the area of a pre-existing cardiac valve, especially by a transapical, transfemoral, trans-septal, subclavian or transaortic percutaneous route, and which permits restoration of a valve function. The release of the thrombogenic elements, such that they deploy peripherally from the prosthesis, in this case makes it possible to reduce paravalvular leaks.

Figure 17:
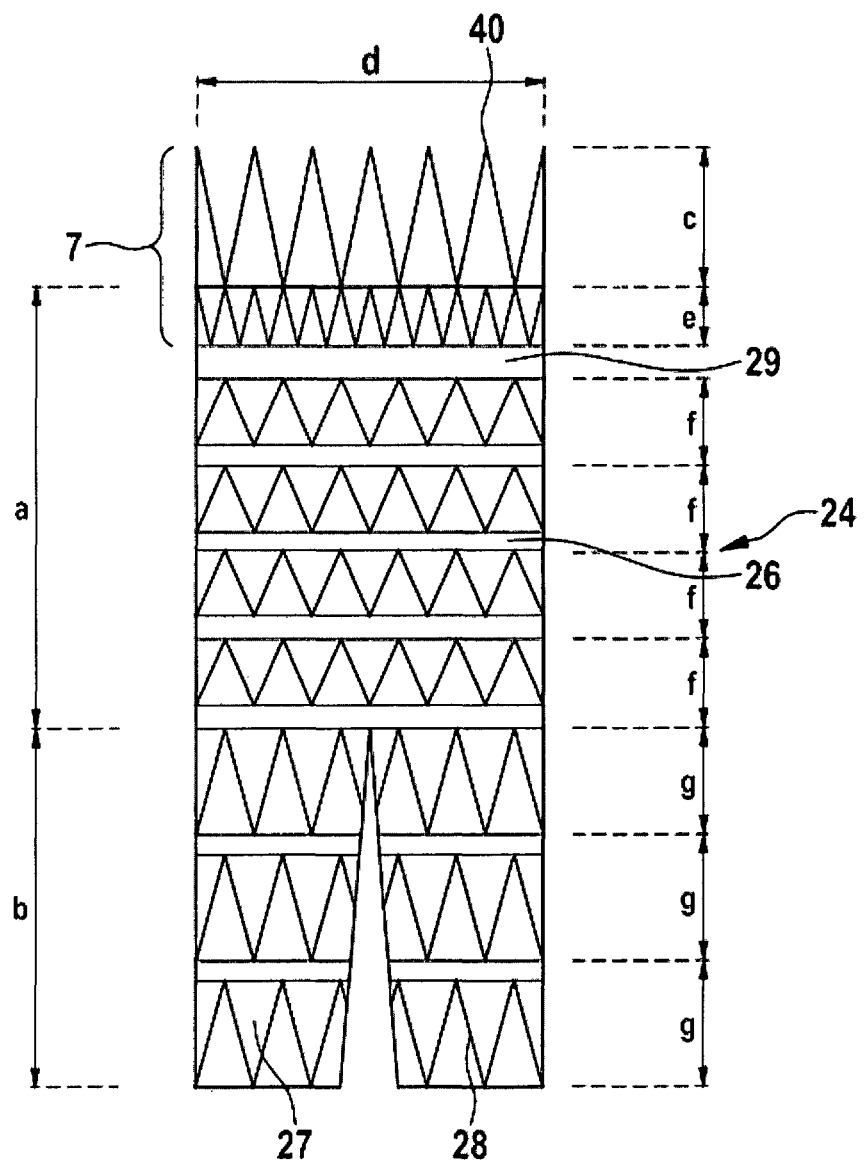
FIG. 17 is a schematic side view of a slightly different prosthesis similar to FIG. 14.

FIG. 17 shows a schematic view of a slightly different trifurcated endoprosthesis similar to FIG. 14. The main body 24 comprises a common tubular section 26 having a length a of about 4 cm. The diameter d of the common tubular section 26 is between 2.2 and 3.8 cm. The legs each have length b of about 3.0 cm. The suprarenal stent 7 has preferably 8 or 10 "peaks" 40. The peaks 40 are all spaced apart in a range from 0.8 cm to 1.2 cm. The suprarenal stent has a total length of about 2.3 cm wherein a proximal end is uncovered i.e. not provided with thrombogenic elements and has a length c of about 1.35 to 1.5 cm. A distal end is provided with thrombogenic elements and has a length e of about 0.5 to 0.6 cm.

The common tubular section 26 has four stent floors each having a length of about 0.7 to 0.8 cm and a proximal area 29 not provided with thrombogenic elements 3. Each leg 27, 28 has 3 stent floors which have a maximal length g of about 0.97 cm.

Figure 18:
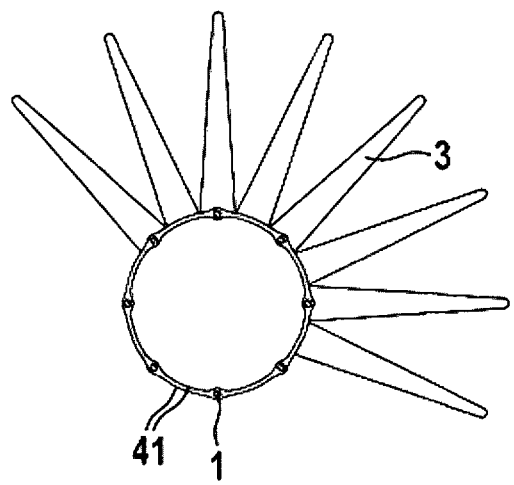
FIG. 18 is a schematic top view of a prosthesis according to the invention.

FIG. 18 shows a top view of a prosthesis according to the invention. The thrombogenic filaments 3 are attached to the prosthesis 1 with two fibres 41. The two fibres are preferably made of PTFE and might be arranged helically around the prosthesis (see FIG. 19 for more details). Therewith, all thrombogenic fibres 3 are fixed to the prosthesis with two fibres 41 only. However, a different number of fibres 41 for fixation might be possible, e.g. 1, 3, 4 or 5.

Figure 19:
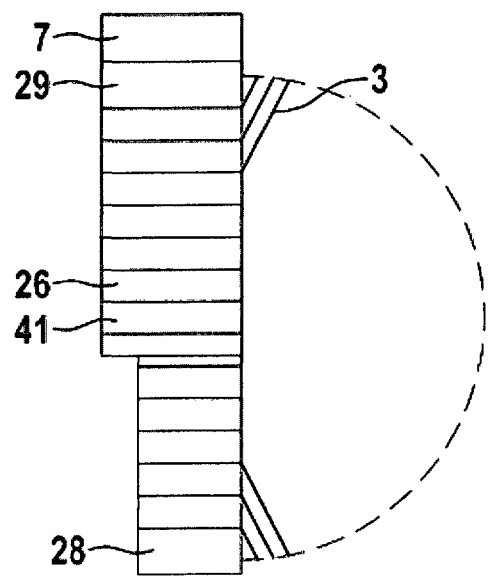
FIG. 19 is a partial side view of a bifurcated or trifurcated prosthesis according to the invention.

FIG. 19 shows a partial schematic view of half of a trifurcated endoprosthesis 1 with a common tubular section 26 and two leg 27, 28 of which only one leg 28 is shown, however. On the proximal edge of the prosthesis is the suprarenal stent. On the outer surface of the common tubular section 26 as well as on the outer surface of the legs 27, 28 are thrombogenic filaments 3 arranged. The length of the thrombogenic filaments is indicated with a dashed line in the form of approximately a semi circle. The length of the thrombogenic filaments 3 is shorter near the proximal and distal edge compared to the centre of the prosthesis.

The invention claimed is:

1. An endoprosthesis comprising:
at least one body part having an outer surface,
wherein thrombogenic elements are arranged at least partially on the outer surface of the at least one body part of the endoprosthesis and, during use, the thrombogenic elements extend a distance away from the outer surface of said at least one body part, and
the endoprosthesis is provided with at least one retaining means for retaining the thrombogenic elements near the surface of said at least one body part;
wherein the at least one retaining means has first and second configurations and is changeable from the first to the second configuration, the at least one retaining means, when in the first configuration, maintains the thrombogenic elements adjacent to the outer surface of the endoprosthesis to assist with installation and implantation of the endoprosthesis, but when the at least one retaining means is changed to the second configuration, the thrombogenic elements are released and thus free to move away from the outer surface and promote thrombosis.

2. The endoprosthesis according to claim 1, wherein at least one area of the outer surface of the at least one body part is provided with thrombogenic elements which are substantially uniformly distributed over said at least one area of the outer surface.

3. The endoprosthesis according to claim 2, wherein the thrombogenic elements are elongated.

4. The endoprosthesis according to claim 2, wherein each thrombogenic element is attached to the body part at at least one anchoring point of the thrombogenic elements.

5. The endoprosthesis according to claim 2, wherein an entire outer surface of the at least one body part is provided with thrombogenic elements.

6. The endoprosthesis according claim 2, wherein thrombogenic elements are arranged at least partially on the outer surface of the at least one body part of the prosthesis and the endoprosthesis is provided with the at least one retaining means for retaining the thrombogenic elements near the surface of said at least one body part.

7. The endoprosthesis according to claim 2 or 1, wherein the thrombogenic elements have at least one loop on a free end opposite an anchoring point for attachment to the at least one retaining means.

8. The endoprosthesis according to claim 7, wherein the loops form substantially an entire length of the thrombogenic elements and an elongate retaining element.

9. The endoprosthesis according to claim 7, wherein the at least one retaining means retains the thrombogenic elements by being in operative connection with the at least one loop of the thrombogenic elements.

10. The endoprosthesis according to claim 9 wherein the at least one retaining means retains at least two thrombogenic elements, by being in operative connection with the at least one loop of the thrombogenic elements.

11. The endoprosthesis according to claim 10, wherein only a single retaining means retains all of the thrombogenic elements.

12. The endoprosthesis according to claim 7, wherein the loop is substantially on a free end opposite an anchoring point.

13. The endoprosthesis according to claim 7, wherein the retaining element passes through a covering zone of at least two loops of two elements.

14. The endoprosthesis according to claim 1, wherein the at least one retaining means is deactivated by being pulled.

15. The endoprosthesis according to claim 14, wherein the at least one retaining means is deactivated by being pulled towards a proximal end of a delivery system.

16. The endoprosthesis according to claim 1, wherein the at least one retaining means is formed of resorbable material and is deactivatable through resorption.

17. The endoprosthesis according to claim 1, wherein the at least one element comprises a tearable envelope and is deactivated through tearing of the envelope.

18. The endoprosthesis according to claim 2 or 1, wherein the thrombogenic elements are provided with at least one medical substance and are designed to deliver said substance.

19. The endoprosthesis according to claim 2 or 1, wherein the body is generally tubular and the thrombogenic elements extend circumferentially around the body.

20. The endoprosthesis according to claim 2 or 1, wherein the body is generally tubular and the thrombogenic elements extend axially along the body.

21. The endoprosthesis according to claim 2 or 1, wherein the outer surface of said at least one body part has at least one edge area which is free from thrombogenic elements.

22. The endoprosthesis according to claim 2 or 1, wherein the thrombogenic elements are attached to said outer surface at a place and have a size chosen such that the thrombogenic elements do not extend over an axial edge of said body part.

23. The endoprosthesis according to claim 2 or 1, wherein the endoprosthesis is constructed as a bifurcated endoprosthesis comprising two body parts.

24. The endoprosthesis according to one of the claim 23, wherein at least one of the main body part and the leg or legs have truncated attachment portion(s) for attachment of the leg or legs to the main body part.

25. The endoprosthesis according to claim 24, wherein the attachment portion(s) have an edge area which is free from thrombogenic elements.

26. The endoprosthesis according to claim 2 or 1, wherein said thrombogenic elements are provided on said main part and said leg(s) are preferably free from thrombogenic elements.

27. The endoprosthesis according to claim 23, wherein the two body parts comprise a main part and an attached or attachable leg.

28. The endoprosthesis according to claim 2 or 1, wherein the endoprosthesis is constructed as a trifurcated endoprosthesis comprising three body parts, and the three body parts comprise a main part and two attached or attachable legs.

29. The endoprosthesis according to claim 28, wherein the three body parts comprise a main part and two attached or attachable legs.

30. The endoprosthesis according to claim 28, wherein at least one of the main body part and the leg or legs have truncated attachment portion(s) for attachment of the leg or legs to the main body part.

31. The endoprosthesis according to claim 2 or 1, of the valve type comprising at least one stent and a valve and being able to be placed in an area of a pre-existing cardiac valve and permitting restoration of a valve function, the thrombosis effect caused by the thrombogenic elements permitting a reduction in paravalvular leaks.

32. A delivery device comprising an endoprosthesis according to claim 2 or 1, wherein the delivery device preferably comprises at least one sheath configured to keep the endoprosthesis compressed during the delivery and wherein the endoprosthesis is arranged such as to be released through a relative movement between the sheath and the endoprosthesis.

33. A delivery device according to claim 32, wherein the device is provided with an activation mechanism for deactivating a retaining element for retaining the thrombogenic elements near the endoprosthesis.

34. A method for implanting an endoprosthesis according claim 2 or 1, which method comprises the steps of positioning the endoprosthesis at the site in such a way as to isolate an aneurysm from the blood flow, or at a site neighbouring a native valve; releasing the thrombogenic elements of the endoprosthesis in such a way that they extend a distance away from the endoprosthesis into the aneurysm.

* * * * *